United States Patent [19]

Shajenko

[11] Patent Number: 4,522,495
[45] Date of Patent: Jun. 11, 1985

[54] OPTICAL SENSING DEVICES
[75] Inventor: Peter Shajenko, Storrs, Conn.
[73] Assignee: The United States of America as represented by the Secretary of the Navy, Washington, D.C.
[21] Appl. No.: 503,913
[22] Filed: Jun. 13, 1983
[51] Int. Cl.$^3$ .............................................. G01B 9/02
[52] U.S. Cl. ..................................... 356/345; 250/227
[58] Field of Search ................. 356/345, 361; 250/227
[56] References Cited

U.S. PATENT DOCUMENTS 4,422,167 12/1983 Shajenko ........................... 73/655 X
4,442,350 4/1984 Rashleigh ............................ 250/227

OTHER PUBLICATIONS

Glatzel et al., "Temperature Measurement Technique Using Fresnel Interference Technique", *IBM Tech. Discl. Bull.*, vol. 20, No. 11A, pp. 4571–4572, 4/78.

*Primary Examiner*—Davis L. Willis
*Assistant Examiner*—Matthew W. Koren
*Attorney, Agent, or Firm*—Robert F. Beers; Arthur A. McGill; Michael J. McGowan

[57] ABSTRACT

Optical sensing devices comprising dual chamber apparatii which use signal and reference light beams together with interferometric methods for detection of physical quantities of interest. The signal part of the chamber experiences the effects of a particular physical quantity to be measured which produces variations in the optical length of the light beam by movement of a mirror, thereby modulating that beam in proportion thereto. Concurrently, the reference beam, of equal pathlength, is passed through an adjacent chamber, isolated from such effects. The modulated signal beam and unmodulated reference beam are then combined to form a fringe pattern, the zero and first order fringes which are superimposed on apertures of an optical fibers, which carry the resultant light beams to a photodetectors for converting the optical signals to proportional electrical signals.

11 Claims, 7 Drawing Figures

OPTICAL SENSING DEVICES

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to very sensitive optical devices for detecting or measuring many physical phenomena using the techniques of optical interferometry. More particularly, this invention relates to a system for sensing a given physical quantity to be measured by applying optical fibers for remote measurement, further permitting the use of multimode optical fibers with all kinds of light sources including white light.

(2) Description of the Prior Art

All physical phenomena are generally measured by sensing one of the physical effects they produce. Consequently, there are a large variety of sensing devices. Very often, however, these devices have not been sufficiently sensitive, safe or simple. With the availability of optical fibers, it became desirable to perform measurements optically to permit simplified remote operation thereby improving sensitivity while reducing size and weight. Recently, a number of optically operated sensing devices using single mode fibers have been disclosed. Single mode operation, however, encounters many implementation difficulties, such as the requirement for a single mode light source such as a laser, the need to maintain light beam polarization, and focusing difficulties and maintenance of focus problems.

The Acousto-Optic Transducer, described in my U.S. Pat. No. 4,188,096 and my Wide-Area Optical Hydrophone, U.S. patent application Ser. No. 277,297, filed, 6/25/81, now U.S. Pat. No. 4,422,167, are optically operated sensing devices for detecting acoustic pressure. They operate free from the above stated difficulties using multimode optical fibers and white light. In these devices the optical fibers are only used to transmit light to and from the sensor while a special sensing element directly modulates the light beam. The light beam is modulated by varying the optical pathlength in one arm of an interferometer. In my Acousto-Optic Transducer, the actual beam length was varied by moving mirrors, while in my Wide-Area Optical Hydrophone, the index of refraction of the medium in which the light beam propagates was varied. Demodulation was performed with an interferometer, where the modulated signal beam was compared with the nonmodulated reference beam.

What is generally needed are sensing devices which can measure a wide range of physical phenomena using the principle of operation of the Acousto-Optic Transducer and the Wide-Area Optical Hydrophone. In addition to inherent high sensitivity, such devices would offer simplicity, low cost, freedom from electro-magnetic interference and safe operation.

SUMMARY OF THE INVENTION

Accordingly, it is a general purpose and object of the present invention to provide a sensing system of simple and rigid construction the sensor portion of which can be modified to reliably measure many physical phenomena with a high degree of sensitivity and hence accuracy.

Another object of subject invention is to provide sensor devices wherein two light beams are exposed to the same environmental conditions but only one of them experiences the effects produced by a particular physical quantity to be measured.

Still another object of subject invention is to provide a sensing system which uses multimode optical fibers to simplify data transmission and reduce the size and weight of the associated telemetry equipment.

A further object of subject invention is to provide a sensing system which may use a variety of light sources including white light thus assuring simplicity of construction and reduction of the costs involved.

A still further object of subject invention is to convert phase modulation into more accurately measurable intensity modulation thereby improving operational stability and reducing phase noise effects where phase information is not critical.

A still further object of subject invention is to provide quadrature operation in a simple and reliable way without a need for quadrature adjustment.

These objects are accomplished with the present invention by providing a sensing system comprising a light source, a first optical fiber for transmitting a beam of light, a beam splitter for producing two beams of light, a dual chambered sensor, a path length adjuster in the reference beam, a beam recombiner, a non-transparent plate, zero ('0') order and a 1st order fringe receiving fibers, '0'order and a 1st order photodetectors and a data processor. The dual chamber sensor uses signal and reference light beams together with interferometric methods for detection of the physical quantity of interest. The signal chamber of the sensor is arranged such that it experiences the effect of the particular physical quantity selected to be measured. The effect produces variations in the optical path length of the signal light beam, thereby phase modulating that beam in proportion thereto. Concurrently, the equal path length reference beam is passed through an adjacent chamber, which is isolated from the effects of the phenomena. The modulated signal beam and unmodulated reference beam are then recombined to form a fringe pattern on the non-transparent plate which separates the center fringe light and focuses it on the aperture of one optical fiber, which carries the resultant light beam to a photodetector for converting the optical signal to an electrical signal. The non-transparent plate does the same with the fringe which is in quadrature relationship with the center fringe, focusing the light on a second optical fiber. The light signals are then converted to electrical signals for processing.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

The optical pathlength of a light beam confined in a chamber can be varied by changing the index of refraction of the optical material filling the chamber. Such variation in optical pathlength results in phase modulation of the beam, i.e., the phase of the light beam is shifted in proportion to an applied signal. Phase modulated signals can be recovered by optical interferometry, which makes phase comparisons between the modulated light beam (signal beam) and unmodulated light beams (reference beam). The detection mechanism involves superposition of both beams to form a fringe pattern, the center fringe and the fringe in quadrature relationship therewith are separately focused on the apertures of two optical fibers in such a way as to convert phase modulations into intensity modulation. Each intensity modulated light beam is subsequently converted to an electrical signal by a photodetector.

The arrangement of both beams in the chamber permits use of white light and multimode optical fibers. There is phase correspondence between both beams thereby lowering the spatial coherence requirement of the light source, and equal path adjustment of the light beams thereby lowers the temporal coherence requirements of the light source. The instant invention, by adjacent positioning of signal and reference beams, provides a device where adverse environmental effects are canceled out, since both beams are simultaneously exposed to such effects.

Figure 2:
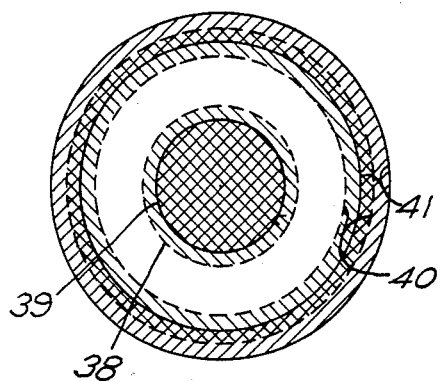
FIG. 2 shows the position of the center fringe and the fringe in quadrature relationship therewith on a non-transparent plate for accomplishing the phase quadrature operation.

Furthermore, the instant invention, by positioning the apertures of both optical output fibers in phase quadrature across the fringes formed by superimposing the beams, provides two signals which are shifted in phase by 90 degrees as shown in FIG. 2. This results in one signal proportional to sin $\rho$ and the other to cos $\rho$, where $\rho$ is a phase shift. By squaring both signals and adding them together electronically, i.e., $\sin^2\rho + \cos^2\rho = 1$, a slable signal output is obtained.

Figure 1:
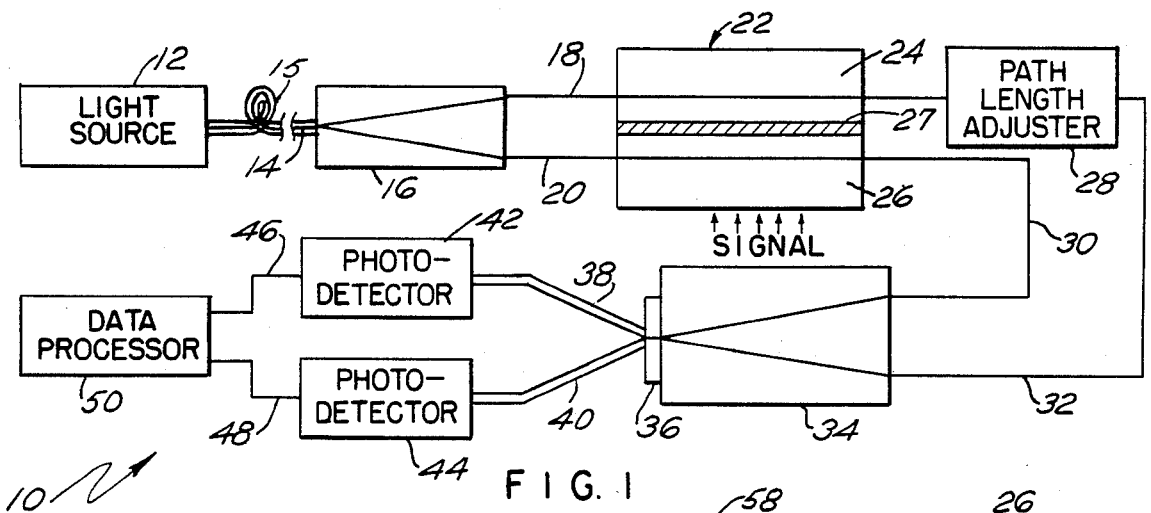
FIG. 1 shows a block diagram of a sensing system built in accordance with the teaching of subject invention.

Referring now to the drawings, FIG. 1 shows a system 10, using a typical sensing device. System 10 includes a light source 12 which directs a light beam 14 along an optical fiber 15. Beam 14 is divided by beam splitter 16 into reference beam 18 and signal beam 20. Beams 18 and 20 next enter sensing device 22, passing through separate chambers 24 and 26 respectively, where they are folded by using movably mounted and fixed mirrors therein for reflections of the beams to increase beam pathlength, thus improving sensitivity. The pathlength of reference beam 18 is adjusted by pathlength adjuster 28 to have the same pathlength as signal beam 20. Signal beam 20 is exposed to the physical quantity to be measured, becoming phase modulated beam 30 while reference beam 18 remains unmodulated becoming beam 32. Beams 30 and 32 are then joined in beam recombiner 34 producing a fringe pattern which includes a center fringe and a fringe in quadrature relationship to the center fringe. The center fringe light energy is positioned by non-transparent plate 36 having a central aperture (preferably circular) corresponding to the center fringe and an annular aperture surrounding the central aperture corresponding to the fringe which is in quadrature relationship with the center fringe. The central aperture in plate 36 is positioned on the aperture of optical fiber 38 while the light energy of the fringe in quadrature relationship in the center fringe is positioned on the aperture of optical fiber 40. The conversion of phase modulation into intensity modulation takes place at this point. Intensity modulated light beams in fibers 38 and 40 are then directed to photodetectors 42 and 44, respectively, where the intensity modulated light beams are converted into proportional electrical signals 46 and 48 respectively. Signals 46 and 48 are then directed to data processor 50, where they are high pass filtered, squared and added together to provide the stable output signal. By using output from only one fiber, the signal retains its phase information, but in such an operation there is a need for adjustment to keep both beams in phase quadrature. Phase quadrature adjustment can be made by applying the technique described in my U.S. patent application Ser. No. 347,112, filed Jan. 29, 1982, which is incorporated herein by reference. This mode of operation also permits measurement of large signals whose value exceeds the value of one fringe shift i.e., more than half the wavelength of light.

FIG. 2 shows the position of optical fiber 38 in relation to the center fringe 39, and the position of optical fiber 40 in relation to fringe 41 which is in quadrature relation with the center fringe 39. When the fringe system shifts in this arrangement, one fiber sees an increase in light intensity, while the other fiber sees a decrease in light intensity, i.e., one provides a sine signal and the other a cosine signal. There are a number of methods for the above-mentioned fringe separation. For example, a non-transparent plate can be used which has a circular aperture for allowing the light intensity from the center fringe 39 and an annular aperture surrounding the circular aperture for allowing the intensity from fringe 41 which is in quadrature relationship with center fringe 39. By proper shift in the fringe pattern across these apertures performance of the system can be optimized.

Figure 3:
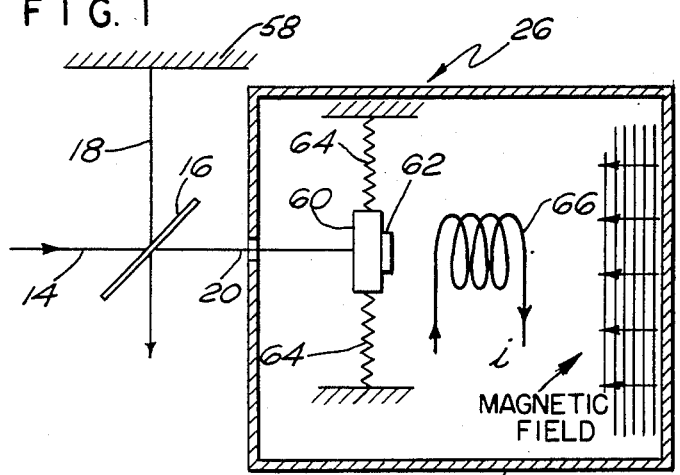
FIG. 3 shows a sensing device suitable for measuring a magnetic field and an electric current.

FIG. 3 shows an embodiment of chamber 26 of a sensing device 22 for measuring a magnetic field or an electric current. Light beam 14 is divided into reference beam 18 and signal beam 20 by beam splitter 16. Mirrors 58 and 60 are set so as to form an equal path interferometer. Mirror 60 is attached to a block of magnetic material 62, which can move due to the influence of an applied magnetic or electric field. The restoring force for mirror 60 is provided by a plurality of springs 64. A magnetic field of any origin or an induced magnetic field due to a current i flowing in coil 66 will produce mirror motion which modulates impinging light beam 20. Magnetic shield 68 can be used to screen the sensing device for zero reading adjustment.

Figure 4:
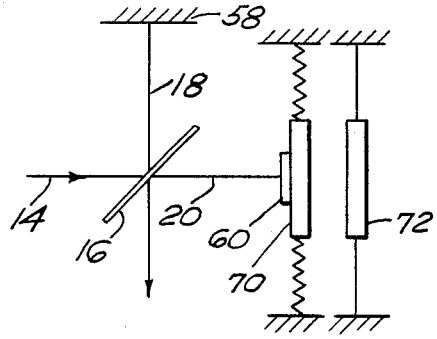
FIG. 4 shows a sensing device suitable for measuring electric voltage.

FIG. 4 shows a sensing device 22 for measuring electric voltage. Here the arrangement of FIG. 3 is used but mirror 60 is instead attached to a metal plate 70, which is electrically insulated but movably mounted by a plurality of springs 64. The second stationary metal plate 72 is rigidly mounted parallel to plate 70. Electric voltage applied between the plates 70 and 72 will set mirror 60 in motion, thereby modulating impinging light beam 20 in proportion thereto.

Figure 5:
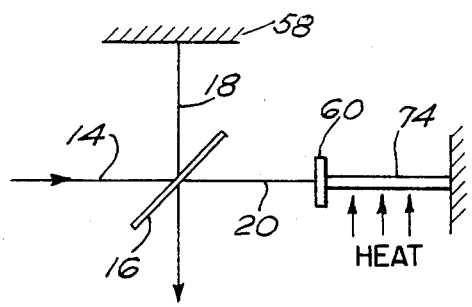
FIG. 5 shows a sensing device suitable for measuring temperature.

FIG. 5 shows a sensing device 22 for measuring temperature. Using a configuration similar to the one shown in FIG. 3, mirror 60 is attached to a temperature sensing element 74 which expands and contracts in response to applied heat, thereby moving mirror 60 producing modulation of impinging light beam 20 in proportion thereto.

Figure 6:
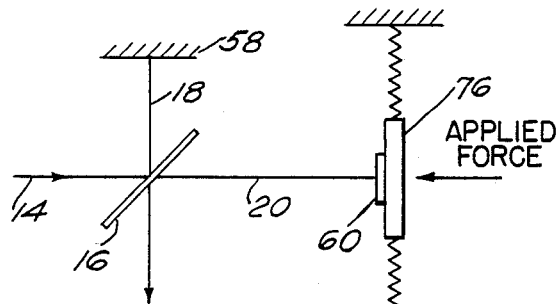
FIG. 6 shows a sensing device suitable for measuring vibrations and/or acceleration.

FIG. 6 shows the configuration of a sensing device 22 for measuring vibration, acceleration, etc. Here mirror 60 is attached to a movably mounted block 76. The motion of block 76 in response to applied forces modulates impinging light beam 20.

Optical sensing devices such as described supra present a new method for sensing many physical phenomena using white light and multimode optical fibers. Reduction in size, weight and costs is expected.

What has been described is a sensing device having a dual chamber sensor and which uses signal and reference light beams together with interferometric methods for detection of a physical quantity of interest. The signal chamber experiences the effects of a particular physical quantity to be measured. Since there are many measurable physical quantities, the number of usable effects is large. All of them however, produce variations in the optical length of the light beam, thereby modulating that beam in proportion thereto. Concurrently, a reference beam, of equal pathlength, is passed through an adjacent chamber, but is isolated from the effects of the phenomena. The modulated signal beam and unmodulated reference beam are then superimposed on the aperture of optical fibers, which carry the resultant light beam to a photodetector for converting the optical signal to proportional electrical signals.

Figure 7:
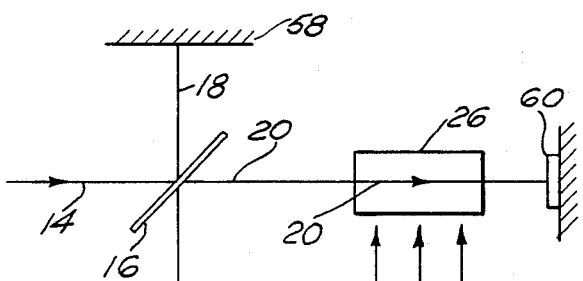
FIG. 7 shows a sensing device for measuring temperature by employing an index of refraction modulation method.

Obviously many modifications and variations of the present invention may become apparent in light of the above teachings. The above figures are some representative examples of sensing devices. Actually, any physical phenomenon which can produce motion of a mirror can be similarly measured. For example, the same principle can be applied in reproduction of recorded signals. The principle can be applied for readout of signals recorded on plates or on magnetic tape where a stylus attached to the mirror modulates the light beams. The results from moving magnetic tape pass through a mirror 60 in the above configuration. Additionally, since modulation of the light beam pathlength can be accomplished by varying the index of refraction of material in which the signal beam propagates, as explained in my co-pending U.S. patent application Ser. No. 277,297 filed 6/25/81, the physical phenomena can also be measured by employing the index of refraction modulation technique. FIG. 7 shows the index of refraction modulation method used for measuring temperature. Here signal chamber 26 of sensing device 22 is filled with an optically transparent material to which heat is applied. The index of refraction of the material changes producing modulation of light beam 20 in proportion thereto.

Many physical phenomena can be measured by applying the index of refraction modulation method, including all kinds of motion, pressure, solubility of materials, etc. Many modifications of the herein described principles are possible to detect, measure, or sense physical phenomena.

In light of the above, it is therefore understood that within the scope of the appended claims, the invention may be practiced otherwise than as specifically described.

What is claimed is:

1. An optical fiber sensing system, for very accurate measurement of the effects of a physical phenomena, comprising:

a light source means for producing a light beam;

a first multimode optical fiber, connected to said light source means, for receiving and transmitting said light beam;

beam splitting means, connected to said first fiber, for receiving said light beam and dividing said light beam into a signal light beam and a reference light beam, each of said signal and reference beams being of equal phase and amplitude;

sensing means for receiving said signal beam and said reference beam from said beam splitting means, said sensing means being divided into a signal chamber and a reference chamber such that said signal beam and said reference beam experience all environmental effects equally, said signal chamber being further arranged so as to further expose only said signal beam to said physical effect to be measured thereby modulating said signal beam in proportion thereto;

path length adjusting means, for receiving said reference beam from the reference chamber of said sensing means and changing the pathlength of said reference light beam to equal the path length of said signal light beam, thus assuring temporal coherence therebetween;

beam recombining means for receiving said signal beam from the signal chamber of said sensing means and said reference beam from said path length adjusting means, said recombining means combining said signal beam and said reference beam in such a way as to form a fringe pattern having at least a center fringe and a fringe in quadrature relationship with the center fringe;

non-transparent plate means, fixedly attached to said recombining means for receiving center fringe and the fringe in quadrature relationship therewith and separating all the light energy of said center fringe from all the light energy of the fringe in quadrature relationship with said center fringe in such a way that 90° phase quadrature is maintained between said signal and reference light beams;

a zero order, multimode optical fiber, attached to said plate means, for receiving and transmitting therethrough said center fringe light energy from said plate means;

a first order, multimode optical fiber, attached to said plate means, for receiving and transmitting therethrough the fringe in quadrature relationship with said center fringe light energy from said plate means;

a first photodetector means, connected to said zero order fiber, for receiving said center fringe light energy and converting said light energy to a proportional zero order electrical signal;

a second photodetector means, connected to said first order fiber, for receiving the fringe in quadrature relationship with said center fringe light energy and converting said light energy to a proportional first order electrical signal; and data processor means, connected to said first and said second photodetectors for receiving said zero order and said first order electrical signals, and processing said signals in such a way as to extract said physical effect measurement therefrom.

2. A sensing system according to claim 1 wherein said light source means further comprises an incandescent bulb.

3. A sensing system according to claim 2 wherein said sensing means further comprises:
   a movably mounted signal mirror for modulating said signal beam by varying the optical path length thereof; and
   a fixedly mounted reference mirror for receiving and reflecting said reference beam.

4. The sensing system of claim 3 wherein said non-transparent plate means includes a central circular aperture for allowing therethrough the light intensity of said center fringe and an annular aperture surrounding the central aperture for allowing therethrough the light intensity of the fringe in quadrature relationship with said center fringe.

5. The sensing system of claim 1 which further includes magnetic materials for responding to changes in the magnetic field to cause modulation of the signal light beam.

6. The sensing system of claim 1 which further includes means to cause modulation of the signal light beam in response to changes in electric currents.

7. The sensing system of claim 1 which includes means for modulating the signal light beam to detect variations in voltage of a system.

8. The sensing system of claim 1 which further includes means for modulating the signal light beam in response to temperature variations in a system.

9. The sensing system of claim 1 which also includes means for modulating the signal light beam in response to vibrations in a system.

10. The sensing system of claim 1 which further includes means for modulating the signal light beam in response to the changes in the applied forces in a system.

11. The sensing system of claim 1 which also includes means for modulating signal light beams to detect changes in the refractive index of a fluid in response to the temperature variation thereof.

* * * * *